(12) United States Patent
Deegan

(10) Patent No.: US 6,500,665 B2
(45) Date of Patent: Dec. 31, 2002

(54) DISPOSABLE CAFFEINE TESTING DEVICE

(76) Inventor: John H. Deegan, 400 Stockade Dr., Kingston, NY (US) 12401

( * ) Notice: Subject to any disclaimer, the term of this patent is extended or adjusted under 35 U.S.C. 154(b) by 51 days.

(21) Appl. No.: 09/804,770

(22) Filed: Mar. 13, 2001

(65) Prior Publication Data

US 2002/0132358 A1 Sep. 19, 2002

(51) Int. Cl.[7] .......................... C12M 1/00; C12M 1/34; G01N 33/53
(52) U.S. Cl. ............... 435/283.1; 435/287.1; 435/25; 435/28; 435/970; 435/805
(58) Field of Search .................. 435/283.1, 25, 435/28, 970, 805, 287.1

(56) References Cited

U.S. PATENT DOCUMENTS

| | | | |
|---|---|---|---|
| 4,868,106 A | 9/1989 | Ito et al. | 435/7 |
| 5,096,813 A | 3/1992 | Krumhar et al. | 435/28 |
| 5,610,072 A | 3/1997 | Scherl et al. | 436/96 |
| 5,660,790 A | 8/1997 | Lawrence et al. | 422/56 |
| 5,801,060 A | 9/1998 | Smith | 436/163 |
| 5,817,454 A | 10/1998 | Harris et al. | 435/4 |
| 5,897,834 A | 4/1999 | Lawrence et al. | 422/56 |
| 6,012,464 A | 1/2000 | Hollowell et al. | 132/202 |

*Primary Examiner*—Louise N. Leary
(74) *Attorney, Agent, or Firm*—Dale J. Ream

(57) ABSTRACT

A device for detecting and indicating the caffeine concentration of a beverage includes a disposable test sheet having a reagent section and a color chart. The reagent section is impregnated with a reagent which, when reacted with caffeine, produces a characteristic chromogenic and color change. These changes vary according to the caffeine concentration of a tested beverage sample. The color chart includes a plurality of color gradations corresponding to ranges of caffeine concentrations and includes numerical indicia corresponding to respective color gradations. The color chart further includes indicia indicative of representative beverages corresponding to respective color gradations and numerical ranges. The color chart may be arranged concentrically about the reagent section or in tabular list form. The test sheet includes a polymeric layer to prevent a beverage sample from soaking through the reagent section.

19 Claims, 4 Drawing Sheets

DISPOSABLE CAFFEINE TESTING DEVICE

BACKGROUND OF THE INVENTION

This invention relates generally to the detection of caffeine in a beverage and, more particularly, to a disposable test sheet that enables a consumer to determine the caffeine concentration of a beverage at the time of consumption and to compare the caffeine concentration to a numeric range and representative beverages within that range.

Consumers have become increasingly concerned about the effects that caffeine may have on their bodies. For example, pregnant women may avoid caffeine due to its teratogenic effect. Others may avoid caffeine because it is a known diuretic. Others simply desire to avoid caffeinated beverages during the evening hours due to its stimulating effect that may lead to insomnia.

Various devices have been proposed in the art for determining the concentration of caffeine in a beverage, such as the dipstick device disclosed in U.S. Pat. No. 5,610,072 to Scherl, et al. Although assumably effective for their intended purposes, the existing devices are not portable and do not provide for a disposable sheet that allows a consumer to determine the caffeine concentration of a beverage sample and to compare an identified numerical range to representative beverages having similar concentrations.

Therefore, it is desirable to have a caffeine testing device that enables a consumer to determine the caffeine concentration of a beverage by comparing a test result color with color gradations on an integral color chart. Further, it is desirable to have a caffeine testing device which enables a consumer to compare the caffeine concentration of a beverage with predetermined concentrations of other beverages.

SUMMARY OF THE INVENTION

A caffeine testing device according to the present invention includes a test sheet constructed of a flexible and disposable material such as cloth, paper, or cardboard. Therefore, the test sheet may be constructed in the form of a napkin, coaster, or the like. The test sheet includes a reagent section on which a consumer may place a sample of a beverage, e.g. a few drops, for testing. The reagent section is impregnated with a reagent which, when reacted with caffeine, produces a characteristic chromogenic change which corresponds to a particular caffeine concentration. This change is observable in that the chromogenic change produces a color that is characteristic of the respective caffeine concentration of the beverage sample.

The test sheet further includes a color chart having a plurality of color gradations corresponding to the possible color variations that may result from a reaction between the reagent and a beverage sample. The color gradations may be arranged as concentric sections surrounding a centrally positioned reagent section or in a more conventional tabular list format. The color chart includes numerical indicia representing the caffeine concentration associated with each respective color gradation. Therefore, a consumer is able to determine a caffeine concentration range of a beverage sample by matching the color of the reagent section with a corresponding color gradation on the color chart. The color chart further includes a list of representative beverages relative to each color gradation and associated caffeine concentration range. Thus, a consumer is able to identify the caffeine concentration of a beverage, the names of other beverages having similar concentrations, as well as the names of alternative beverages having lower concentrations.

Therefore, a general object of this invention is to provide a caffeine testing device for detecting and displaying the caffeine concentration of a beverage.

Another object of this invention is to provide a caffeine testing device, as aforesaid, having a color-coded chart for indicating caffeine concentration ranges for comparison with the color of a test result.

Still another object of this invention is to provide a caffeine testing device, as aforesaid, which is portable and disposable.

Yet another object of this invention is to provide a caffeine testing device, as aforesaid, in which the color observed in a test area varies according to the concentration of caffeine in a tested beverage sample.

A further object of this invention is to provide a caffeine testing device, as aforesaid, which includes an impermeable polymeric layer opposite the reagent section so as to prevent a beverage sample from soaking through the reagent section.

A still further object of this invention is to provide a caffeine testing device, as aforesaid, in which the reagent section is constructed of an absorbent material.

Other objects and advantages of this invention will become apparent from the following description taken in connection with the accompanying drawings, wherein is set forth by way of illustration and example, embodiments of this invention.

DESCRIPTION OF THE PREFERRED EMBODIMENT

Figure 1:
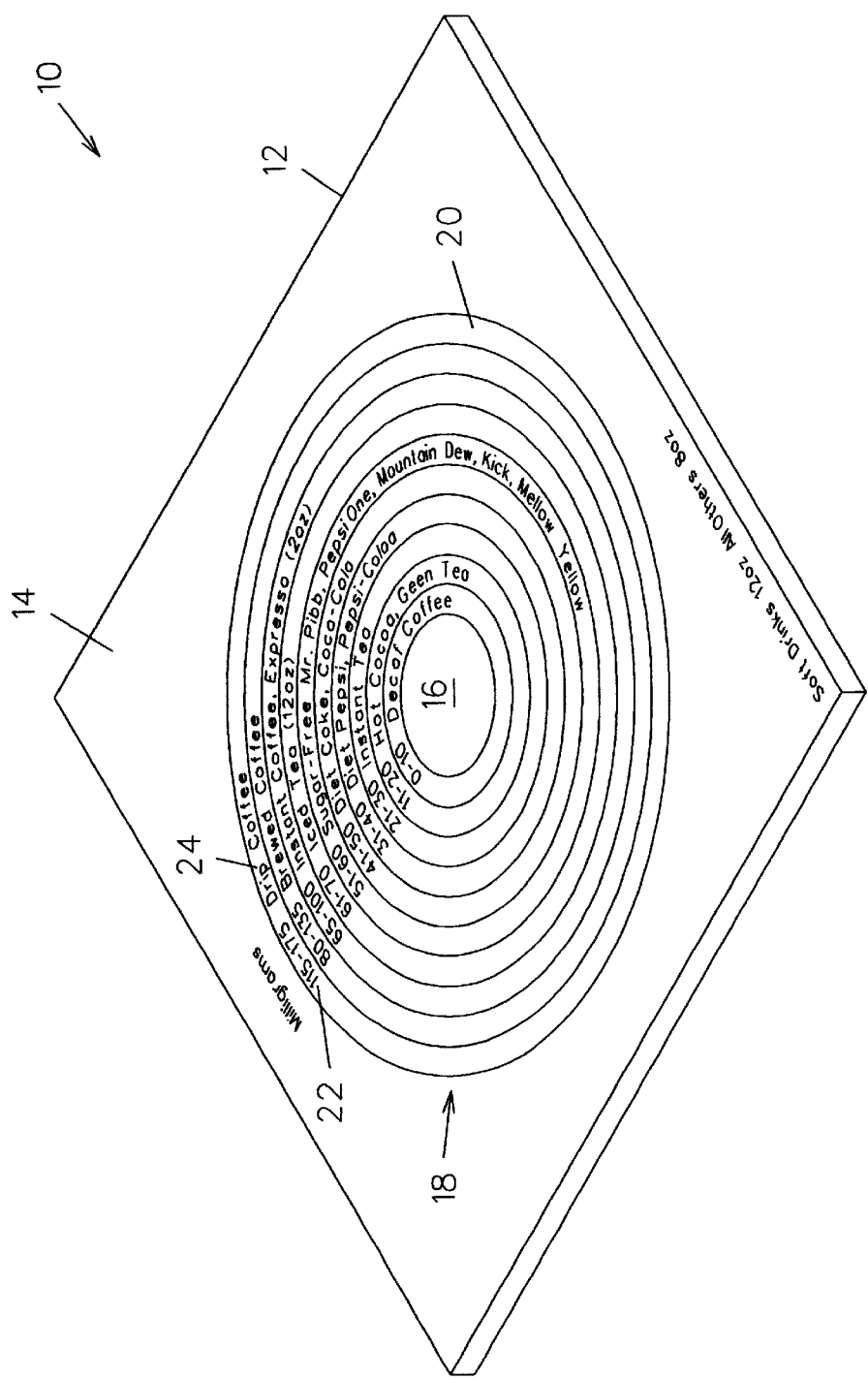
FIG. 1 is a perspective view of a caffeine testing device according to one embodiment of the present invention.

A caffeine testing device according to the present invention will now be described in detail with reference to FIGS. 1–4b. A caffeine testing device 10 according to one embodiment includes a test sheet 12 constructed of a disposable material such as cardboard although paper, cloth, foam, cork, rubber, or other similar materials would also be suitable. Preferably, the test sheet 12 is constructed in the form of a coaster for supporting a beverage container (FIG. 1), although the test sheet 12 may also be constructed in the form of a napkin or the like (FIG. 3).

The test sheet 12 includes a reagent section 16 and a color chart 18. The reagent section 16 includes a circular configuration and is positioned in the center of a front side 14 of the test sheet 12. This is the section upon which a sample of a beverage may be placed for testing its caffeine concentration. The reagent section 16 is impregnated with a reagent which, when reacted with caffeine, produces a characteristic color due to a respective chromogenic change that varies according to the concentration of caffeine in a beverage test sample.

Several reagents are known which can be used in the reagent section 16. One possibility is for the reagent section 16 to include a xanthine oxidase enzyme coupled with a horseradish peroxidase enzyme, a buffer (pH 7.5 phosphate buffer), and a chromogen which produces a color change on the reagent section when a coupled enzymatic reaction occurs. The reaction of $O_2$ and caffeine in the presence of the xanthine oxidase enzyme produces hydrogen peroxide ($H_2O_2$) and oxidized caffeine. The $H_2O_2$ reacts with the chromogen in the presence of the peroxidase enzyme to produce an oxidized form of the chromogen whose color varies with the concentration of hydrogen peroxide and thus caffeine.

In another possibility for the reagent, the reagent section 16 includes monoclonal antibodies reactive against caffeine, a caffeine conjugate labeled with flavin adenine dinucleotide (FAD), apoglucose oxidase which reacts with unbound caffeine conjugate, a chromogen buffer, and peroxidase. Competitive binding between caffeine and caffeine conjugate results in increased amounts of hydrogen peroxide being produced by the glucose oxidase reaction. As was described previously, the color of the chromogen will vary according to the concentration of hydrogen peroxide and thus according to the caffeine concentration.

The color chart 18 on the test sheet 12 is arranged as concentric sections 20 surrounding the reagent section 16 (FIG. 1). Each concentric section 20 includes a particular color gradation characteristic of a possible chromogenic reaction. Preferably, the concentric sections are ordered successively with the color corresponding to the smallest caffeine concentration being closest to the reagent section 16 and the color corresponding to the largest caffeine concentration being furthest from the reagent section 16. The color chart 18 includes first indicia 22 in the form of numeric ranges indicating the range of caffeine concentrations indicated by a respective color. These numeric ranges are imprinted upon said test sheet 12 within respective concentric sections 20 of the color chart 18. The color chart 18 further includes second indicia 24 in the form of names of beverages representative of corresponding caffeine concentration ranges. Each list of beverage names is imprinted within appropriate concentric sections 20. For example, "Drip Coffee" is imprinted within the outermost concentric section which corresponds to a caffeine concentration in the 115–175 mg. range. Therefore, a consumer may match the color of the reagent section with a matching color gradation and be informed immediately as to other beverages sharing the same caffeine concentration range as well as to alternative beverages having different caffeine concentrations.

It should be understood that the reagent section 16 and color chart 18 are preferably positioned on the same side of the test sheet 12 although being positioned on opposing sides would also be suitable.

Figure 2A:
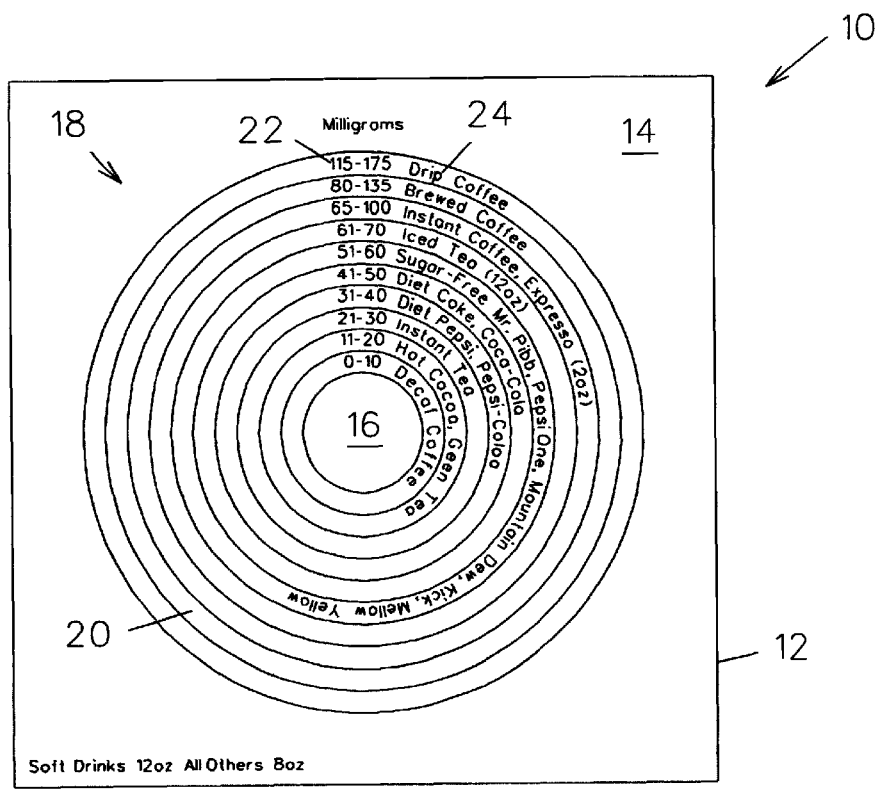
FIG. 2a is a top view of the device as in FIG. 1.
Figure 2B:
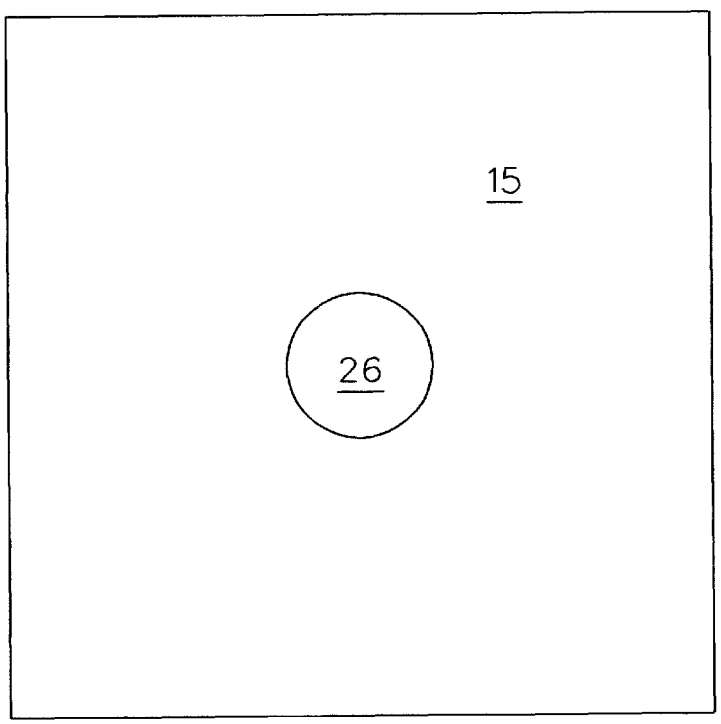
FIG. 2b is bottom view of the device as in FIG. 1.
Figure 3:
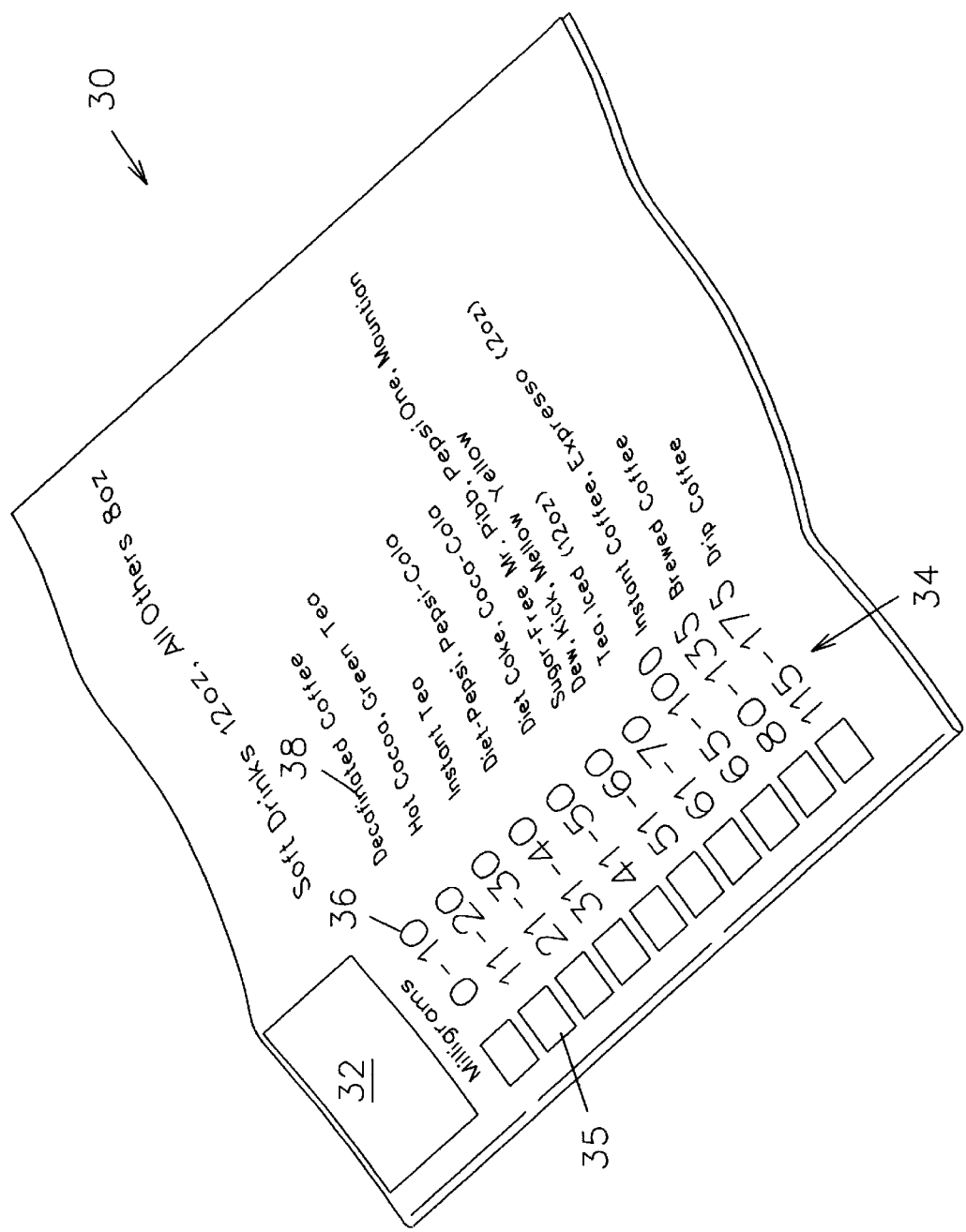
FIG. 3 is a perspective view of a caffeine testing device according to another embodiment of the present invention.

The bottom side 15 of the test sheet 12 includes an impermeable layer 26 constructed of a non-absorbent polymeric material positioned directly opposite the reagent section 16 (FIG. 2b). This construction prevents a beverage sample from soaking through the reagent section 16 and potentially staining a tablecloth or any other material positioned beneath the test sheet 12 during use.

In use, a user may use a spoon or straw to deposit a few drops of a beverage upon the reagent section 16 on the front side 14 of the test sheet 12. The chemical reaction between the reagent and caffeine causes a chromogenic change that yields an observable color. By matching the color produced in the reagent section 16 with a corresponding color gradation in the color chart 18 that is also positioned on the front side 14 of the test sheet 12, the user may determine the caffeine concentration range of the tested beverage. The user may also be informed of alternative beverages and their relative caffeine concentrations.

Figure 4A:
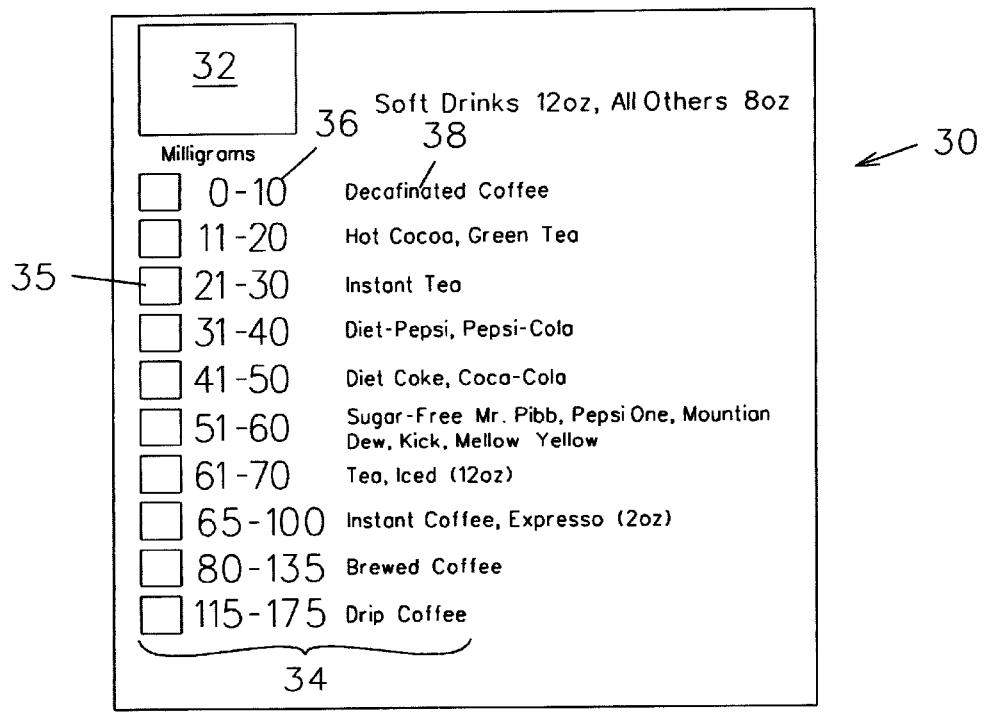
FIG. 4a is a top view of the device as in FIG. 3 in a folded configuration.
Figure 4B:
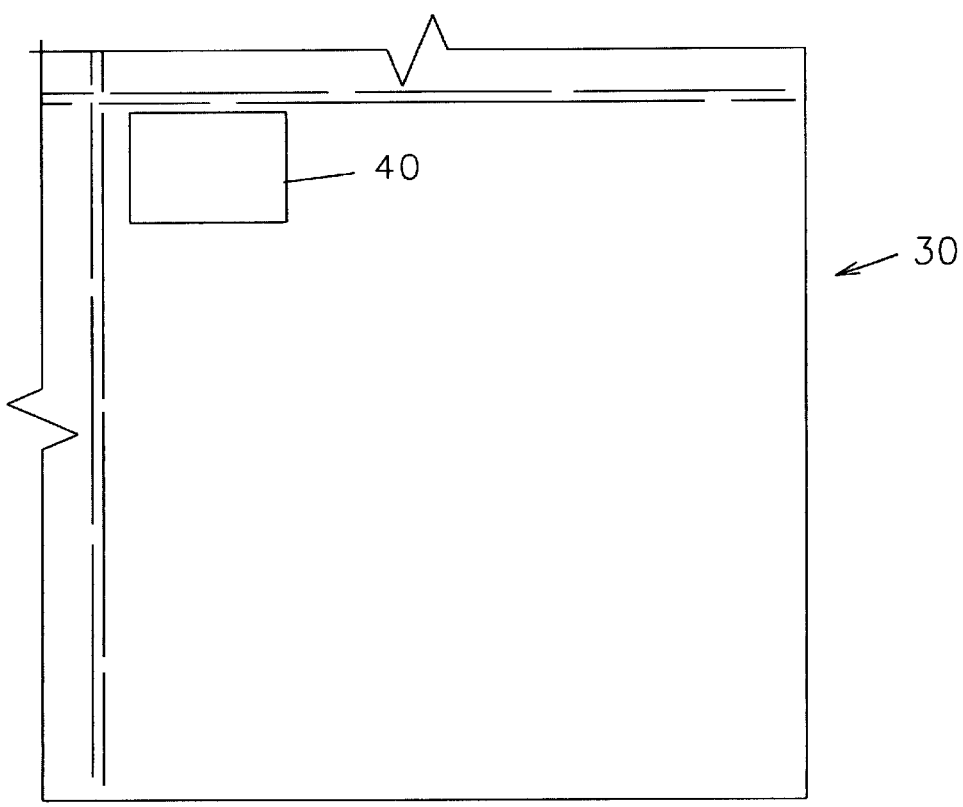
FIG. 4b is a fragmentary bottom view of the device as in FIG. 3 in an unfolded configuration.

Another embodiment 30 of this invention is shown in FIGS. 3–4b and includes a construction substantially similar to that described previously except as specifically noted below. This embodiment 30 is constructed in the form of a flexible paper napkin that may be opened to reveal four quadrants, as is conventional. A reagant section 32 is positioned in the upper left-hand corner of a front side of a first napkin quadrant. This reagent section 32 operates in the same manner as previously described. This embodiment 30 also includes a color chart 34 arranged in a tabular list format in which the color gradations 35 extend along the left side of the front side of the first quadrant so that they are immediately below the reagant section 32, making comparisons easy. Respective first indicia 36 of numerical ranges are imprinted adjacent appropriate color gradations 35. Respective second indicia 38 of representative beverage names are imprinted adjacent corresponding first indicia 36. An impermeable, non-absorbent polymeric layer 40 is positioned opposite the reagent section 32 as seen when the napkin is unfolded (FIG. 4b).

It is understood that while certain forms of this invention have been illustrated and described, it is not limited thereto except insofar as such limitations are included in the following claims and allowable functional equivalents thereof.

Having thus described the invention, what is claimed as new and desired to be secured by letters patent is as follows:

1. A device for detecting and indicating the concentration of caffeine in a beverage, comprising:
    a disposable test sheet constructed in the form of a napkin;
    a reagent section on said test sheet adapted to receive a sample of a beverage thereon, said reagent section being impregnated with a reagent which, when reacted with caffeine, produces a characteristic color corresponding to a characteristic chromogenic change in said reagent section which varies according to the concentration of caffeine in said beverage sample; and
    a color chart on said test sheet having color gradations for comparison with said characteristic color produced in said reagent section.

2. The device as in claim 1 wherein said reagent section is positioned on one side of said test sheet and said color chart is positioned on said one side of said test sheet adjacent said reagent section.

3. The device as in claim 1 wherein said reagent section is centrally positioned on said test sheet and said color gradations of said color chart are arranged in concentric sections about said reagent section.

4. The device as in claim 1 wherein said color chart is arranged in tabular form with said color gradations ordered from lowest to highest caffeine concentrations.

5. The device as in claim 1 wherein said color chart includes a first indicia indicative of numerical ranges associated with caffeine concentrations corresponding to respective color gradations.

6. The device as in claim 5 wherein said color chart includes a second indicia indicative of representative beverages having caffeine concentrations corresponding to respective color gradations.

7. The device as in claim 1 wherein said reagent includes an oxidase enzyme, a peroxidase enzyme, and a reactive chromogen which when oxidized in the presence of caffeine produces said characteristic chromogenic change.

8. The device as in claim 1 wherein said reagent utilizes a xanthine oxidase enzyme reaction to produce said characteristic chromogenic change.

9. The device as in claim 1 wherein said test sheet is constructed in the form of a coaster.

10. The device as in claim 1 further comprising an impermeable polymeric layer positioned on a side of said test sheet opposite said reagent section so as to prevent said sample from soaking through said reagent section.

11. A device for testing and indicating the concentration of caffeine in a beverage sample, comprising:

a test sheet constructed in the form of a coaster and having a reagent section on one side of said test sheet adapted to receive a beverage sample thereon, said reagent section being impregnated with a reagent which, when reacted with caffeine, produces a characteristic color corresponding to a characteristic chromogenic change in said reagent section which varies according to the concentration of caffeine in said beverage sample;

a color chart on said one side of said test sheet adjacent said reagent section, said color chart including a plurality of color gradations for comparison with said characteristic color produced in said reagent section and a first indicia indicative of numerical ranges associated with caffeine concentrations represented by respective color gradations.

12. The device as in claim 11 wherein said reagent section is centrally positioned on said test sheet and said color gradations of said color chart are arranged in concentric sections about said reagent section.

13. The device as in claim 11 wherein said test sheet is constructed in the form of a disposable paper napkin.

14. The device as in claim 11 wherein said color chart includes a second indicia indicative of representative beverages having caffeine concentrations corresponding to respective color gradations.

15. The device as in claim 11 wherein said color gradations and corresponding first indicia of said color chart are arranged in tabular form.

16. The device as in claim 11 further comprising an impermeable polymeric layer positioned on another side of said test sheet opposite said reagent section so as to prevent said sample from soaking through said reagent section.

17. The device as in claim 11 wherein said reagent includes an oxidase enzyme, a peroxidase enzyme, and a reactive chromogen which when oxidized in the presence of caffeine produces said characteristic chromogenic change.

18. The device as in claim 11 wherein said reagent utilizes a xanthine oxidase enzyme reaction to produce said characteristic chromogenic change.

19. A device for detecting and indicating the concentration of caffeine in a beverage, comprising:

a disposable test sheet;

a reagent section on said test sheet adapted to receive a sample of a beverage thereon, said reagent section being impregnated with a reagent which, when reacted with caffeine, produces a characteristic color corresponding to a characteristic chromogenic change in said reagent section which varies according to the concentration of caffeine in said beverage sample;

a color chart on said test sheet having color gradations for comparison wit said characteristic color produced in said reagent section, said color chart comprising:

a first indicia indicative of numerical ranges associated with caffeine concentrations corresponding to respective color gradations; and a second indicia indicative of representative beverages having caffeine concentrations corresponding to respective color gradations.

* * * * *